(12) United States Patent
Pan et al.

(10) Patent No.: US 12,693,289 B2
(45) Date of Patent: Jul. 28, 2026

(54) APPLICATION OF COMPOUNDS IN THE PREPARATION OF REAGENTS FOR DOWN-REGULATION OF RUNX2

(71) Applicant: Geneheal Biotechnology Co., Ltd., Guangzhou (CN)

(72) Inventors: Wuguang Pan, Guangzhou (CN); Wei Zhu, Guangzhou (CN)

(73) Assignee: Geneheal Biotechnology Co., Ltd., Guangzhou (CN)

( * ) Notice: Subject to any disclaimer, the term of this patent is extended or adjusted under 35 U.S.C. 154(b) by 493 days.

(21) Appl. No.: 18/200,591

(22) Filed: May 23, 2023

(65) Prior Publication Data

US 2023/0288401 A1 Sep. 14, 2023

Related U.S. Application Data

(63) Continuation-in-part of application No. PCT/CN2021/131753, filed on Nov. 19, 2021.

(30) Foreign Application Priority Data

Nov. 24, 2020 (CN) .......................... 202011332972.2

(51) Int. Cl.
| | |
|---|---|
| *A61P 35/00* | (2006.01) |
| *A61K 31/5383* | (2006.01) |
| *A61K 45/06* | (2006.01) |
| *G01N 33/50* | (2006.01) |

(52) U.S. Cl.
CPC ...... *G01N 33/5011* (2013.01); *A61K 31/5383* (2013.01); *A61K 45/06* (2013.01); *A61P 35/00* (2018.01)

(58) Field of Classification Search
CPC ...... A61P 35/00; A61K 31/5383; A61K 45/06
See application file for complete search history.

(56) References Cited

FOREIGN PATENT DOCUMENTS

| | | |
|---|---|---|
| CN | 105849110 A | 8/2016 |
| CN | 109996544 A | 7/2019 |
| WO | 2018023113 A1 | 2/2018 |
| WO | WO-2020010227 A1 * | 1/2020 ........... C07D 471/04 |
| WO | WO-2020128534 A1 * | 6/2020 ........... A61K 31/713 |

OTHER PUBLICATIONS

International Search Report of PCT Patent Application No. PCT/CN2021/131753 issued on Feb. 17, 2022.

Wang, Jianan et al., PKMYT1 is Associated with Prostate Cancer Malignancy and may Serve as a Therapeutic Target, Gene, Mar. 29, 2020, pp. 1-7, vol. 744.

Shinde, Aparna et al., Spleen Tyrosine Kinase-Mediated Autophagy is Required for Epithelial-Mesenchymal Plasticity and Metastasis in Breast Cancer, Cancer Research, Apr. 15, 2019, pp. 1831-1843, vol. 79, No. 8.

Serafin, Valentina et al., SYK Targeting Represents a Potential Therapeutic Option for Relapsed Resistant Pediatric ETV6-RUNX1 B-Acute Lymphoblastic Leukemia Patients, International Journal of Molecular Sciences, Dec. 7, 2019, pp. 1-8, vol. 20.

P. Heinrich Stahl et al., Handbook of Pharmaceutical Salts: Properties, Selection, and Use, International Union of Pure and Applied Chemistry (IUPAC), Aug. 2002.

* cited by examiner

*Primary Examiner* — Nelson B Moseley, II
*Assistant Examiner* — Dennis J Sullivan

(57) ABSTRACT

The present invention discloses application of compounds in the preparation of reagents for down-regulation of Runx2. The inventors have confirmed through computational studies and disease models that Fostamatinib, Regorafenib and melatonin can significantly down-regulate the expression of Runx2, and have a significant targeted therapeutic effect on cancers with abnormally high expression of Runx2, and are efficient reagents for reducing the expression of Runx2. Especially the Runx2 expression down-regulation reagent used in the laboratory.

8 Claims, 5 Drawing Sheets

APPLICATION OF COMPOUNDS IN THE PREPARATION OF REAGENTS FOR DOWN-REGULATION OF RUNX2

CROSS-REFERENCE TO RELATED APPLICATIONS

The present application is a continuation-in-part application of PCT application No. PCT/CN2021/131753 filed on Nov. 19, 2021, which claims the benefit of Chinese Patent Application No. 202011332972.2 filed on Nov. 24, 2020. The contents of all of the aforementioned applications are incorporated by reference herein in their entirety.

FIELD OF THE INVENTION

The present invention relates to a method for treating tumor by down-regulating RUNX2 expression.

BACKGROUND OF THE INVENTION

Runx2 is a recognized as a transcription factor that plays an important role in the transformation of bone marrow mesenchymal stem cells into osteoblasts. In vitro and in vitro studies have shown that it can participate in bone metabolism, ectopic calcification of the cardiovascular system, abnormal development of teeth, tumor and organ fibrosis and other diseases through various signal transduction pathways such as bone morphogenetic protein/Smads, mitogen-activated protein kinase signaling pathway. The specific mechanism of action of Runx2 in the occurrence, development and prognosis of diseases has not been fully understood, and the treatment of clinical diseases with Runx2 as a target may become a research hotspot. Studies have shown that Runx2 is highly expressed in a variety of tumors, such as breast cancer, lung cancer, lung adenocarcinoma, prostate cancer, multiple myeloma, and malignant lobed tumors of the breast, which directly affects the progression of tumors.

Tumors seriously endanger people's health, and different tumors have different responses to the same drug. In order to improve the efficacy and reduce side effects, it has become a consensus of tumor treatment to formulate a reasonable medication scheme based on the phenotype of the tumor.

Fostamatinib is the prodrug of the active metabolite R406 of the spleen tyrosine kinase (SYK) inhibitor, DrugBank ID: DB12010, CAS number: 945745-48-2, has a variety of medical therapeutic effects, by developed by Rigel Pharmaceuticals of the United States, it is used for the treatment of thrombocytopenia, especially for adult patients with chronic immune thrombocytopenia (ITP) who have not been well relieved by previous treatment regimens.

Regorafenib, DrugBank ID: DB08896, CAS number: 755037-03-7, is a variety of small molecule inhibitors of intracellular kinases bound to cell membranes that are associated with normal cell function and pathological processes such as tumorigenesis, tumor angiogenesis, and maintenance of tumor microenvironment. In vitro biochemical or cellular analysis, ragorafenib or its main human active metabolites M-2 and M-5 inhibit RET, VEGFR1, VEGFR2, VEGFR3, KIT, PDGFR-alpha, PDGFR-beta, FGFR1, FGFR2, TIE2, DDR2, TrkA, Eph2A, RAF-1, BRAF, BRAFV600E at Regorafenib concentrations, SAPK2, PTK5 and Abl. In vivo models, ragorafenib showed antiangiogenic activity in rat tumor models and inhibition of tumor growth as well as antimetastatic activity in several mouse xenograft models, including some human colorectal cancers. Regorafenib has relatively large side effects, and its approved clinical use is for the treatment of patients with metastatic colorectal cancer who have previously received fluorouracil, oxaliplatin, and irinotecan-based chemotherapy, and who have previously received or are not candidates for anti-VEGF therapy and anti-EGFR therapy (RAS wild type); For the treatment of patients with locally advanced, unresectable or metastatic gastrointestinal stromal tumors who have previously received imatinib mesylate and sunitinib malate; For the treatment of hepatocellular carcinoma that has previously been treated with sorafenib.

Melatonin (MT) is one of the hormones secreted by the pineal gland of the brain, DrugBank ID: DB01065, CAS number: 73-31-4, also known as pineal gland, melatonin, melatonin. MT has strong neuroendocrine immunomodulatory activity and free radical scavenging antioxidant capacity.

SUMMARY OF THE INVENTION

It is of great importance to develop new applications for existing compounds.

The technical solution adopted in the present disclosure is as follows:

The first aspect of present invention provides:

A method for treating tumor of a patient, comprising:

a) obtaining a sample from the patient with a tumor;

b) determining the level of Runx2 in the sample; and c) diagnosing the patient as being likely to be responsive to a treatment compound if the level of Runx2 in the sample is significantly higher than a reference level of the Runx2;

d) administering to the patient in need thereof with a therapeutically effective amount of the compound, said compound is selected from Fostamatinib and acceptable salts thereof, Regorafenib and acceptable salts thereof, and melatonin and acceptable salts thereof.

In some embodiments, higher expression of Runx2 is defined as a relatively significantly higher expression than normal tissue, such as 1.5 times, 2 times, 3 times, 5 times or more higher than normal tissue of the patient.

In some embodiments, further comprising administering a known active ingredient with therapeutic effect on the tumor.

In some embodiments, the salt is an acid or base addition salt of the compound.

In some embodiments, said acid is selected from a group consist of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid; the base is a hydroxide of the alkali metal, alkaline earth metal.

The second aspect of present invention, providing:

Use of compositions in the preparation of anti-tumor drug, the active ingredient of said composition is selected from one, two, three of Fostamatinib and acceptable salts thereof, Regorafenib and acceptable salts thereof, and melatonin and acceptable salts thereof.

In some embodiments, the tumor is a tumor with a high expression of Runx2.

In some embodiments, the tumor is selected from breast cancer, lung cancer, lung adenocarcinoma, prostate cancer, multiple myeloma, malignant lobular tumors of the breast.

In some embodiments, said composition include at least one extra known active ingredient with therapeutic effects on tumors.

In some embodiments, the salt is an acid or base addition salt of the compound.

In some embodiments, said acid is selected from a group consist of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid; the base is a hydroxide of the alkali metal, alkaline earth metal.

The third aspect of present invention, providing:

Use of compositions in the preparation of agents modulating Runx2 expression, the active ingredient of the composition is selected from Fostamatinib and acceptable salts thereof, Regorafenib and acceptable salts thereof, and melatonin and acceptable salts thereof.

In some embodiments, the salt is an acid or base addition salt of the compound.

In some embodiments, said acid is selected from a group consist of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid; the base is a hydroxide of the alkali metal, alkaline earth metal.

In some embodiments, the use is for experimental use.

Beneficial Effect

Through computational studies and disease models, the inventors have shown that:

Fostamatinib, Regorafenib and melatonin can significantly down-regulate the expression of Runx2, has a significant targeted therapeutic effect on cancers with abnormally high expression of Runx2, and is an efficient Runx2 expression down-regulating reagent, especially for the laboratory use.

By administering to the patient in need thereof with a compound selected from Fostamatinib, Regorafenib, and melatonin, or in combination, or in combination with a known antitumor drug, efficacy can be effectively improved and/or side effects be reduced.

Acceptable salts of Fostamatinib, Regorafenib or melatonin, in vivo or cellular environment, can produce the same or similar effects as Fostamatinib, Regorafenib or melatonin, and also have corresponding curative effects or effects.

DETAILED DESCRIPTION OF THE EMBODIMENTS

Figure 1:
FIG. 1 shows the expression level of RUNX2 protein after Fostamatinib acts on lung cancer cells A549 and lung cancer cell H1299 for 8 h, respectively.

As used herein, the term "high expression" has the meaning well known in the art, and refers to the expression which is significantly increased as compared to that of a normal tissue. In general, the expression is 1.5 times, 2 times, 3 times, 5 times or more than that of normal tissues.

Pharmaceutically acceptable salts of the compounds can be synthesized from parent compounds by conventional chemical methods, such as those in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. In general, these salts can be prepared by the reaction of the free base and acid of the compound in water or an organic solvent or a mixture of the two; Typically, non-aqueous media such as ether, ethyl acetate, ethanol, isopropanol or acetonitrile are used.

Acid addition salts can be made by various acids (inorganic and organic acids). Embodiments of acid addition salts include a salt made by a compounds reacted with an acid, said acid is selected from a group consist of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethane-sulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acid.

Through computational studies and preliminary experimental studies of related disease models, the inventors have confirmed that:

1) Fostamatinib, Regorafenib and melatonin can significantly down-regulate the expression of Runx2, has a significant targeted therapeutic effect on cancers with abnormally high expression of Runx2, and is an efficient Runx2 expression down-regulating reagent, especially for the laboratory use.

2) By use of one of Fostamatinib, Regorafenib, and melatonin, or in combination, or in combination with a known antitumor drug, efficacy can be effectively improved and/or side effects be reduced.

3) Acceptable salts of Fostamatinib, Regorafenib or melatonin, in vivo or cellular environment, can produce the same or similar effects as Fostamatinib, Regorafenib or melatonin, and also have corresponding curative effects or effects.

The preliminary experiment is as follows:

Effects of Fostamatinib on Protein and mRNA Expression of Runx2 in Tumor Cells

Cells are seeded in medium dishes (6 cm), cultured overnight, when the cell confluency is 80%, the original medium is discarded, PBS rinses the cells, and then replaced with Fostamatinib containing a final concentration of 10 uM or other concentrations, after 6-12 hours, the cells are harvested, RNA and protein liquid are extracted, and the protein and mRNA expression changes of RUNX2 are detected by Western blot and qPCR experiments, respectively.

The experimental results are shown in FIGS. 1-5, wherein:

FIG. 1 shows that after treated with Fostamatinib for 8 hours respectively, the protein expression level of RUNX2 of lung cancer cells A549 and lung cancer cell H1299 tends to decrease (in FIG. 1, F represents Fostamatinib).

Figure 2:
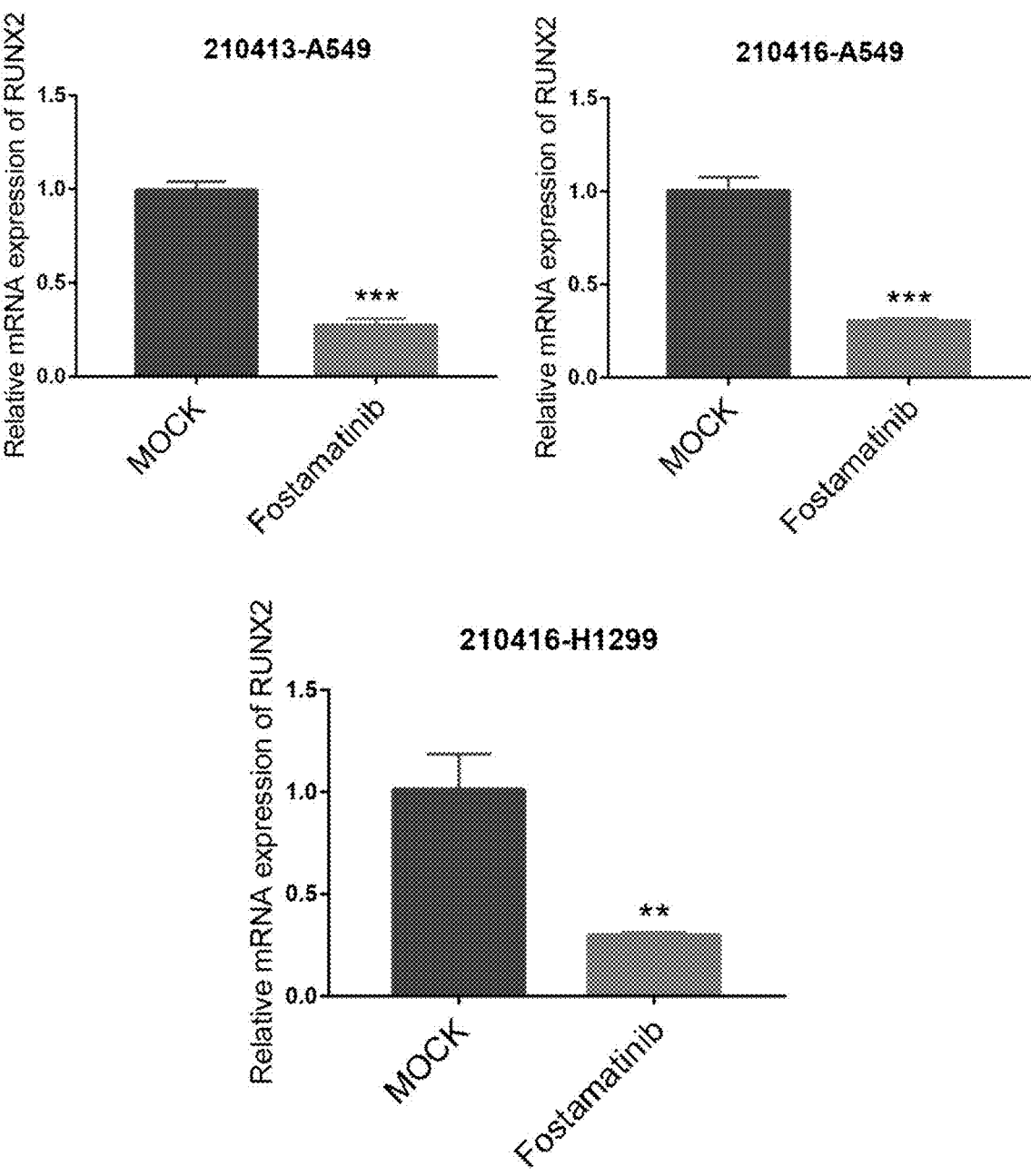
FIG. 2 shows the expression level of RUNX2 mRNA after Fostamatinib acts on lung cancer cells A549 and lung cancer cell H1299 for 8 h, respectively.

FIG. 2 shows that after treated with Fostamatinib for 8 hours respectively, the mRNA expression level of RUNX2 of lung cancer cells A549 and lung cancer cell H1299 decreases significantly.

Figure 3:
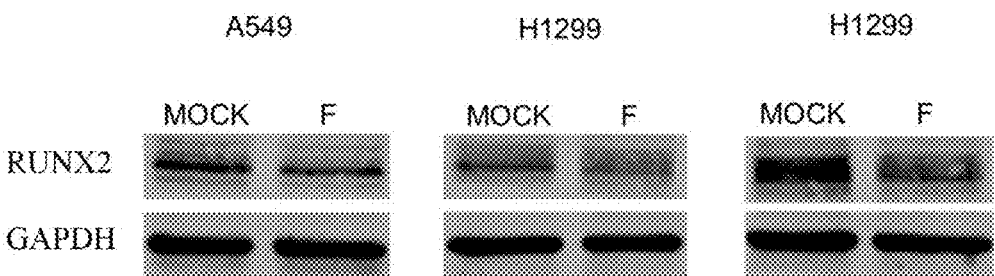
FIG. 3 shows the expression level of RUNX2 protein after Fostamatinib acts on lung cancer cells A549 and lung cancer cell H1299 for 6 h, respectively.

FIG. 3 shows that after treated with Fostamatinib for 6 hours respectively, the protein expression level of RUNX2 of lung cancer cells A549 and lung cancer cell H1299 down-regulated a certain trend (in the figure., F indicates Fostamatinib, the antibody has been changed).

Figure 4:
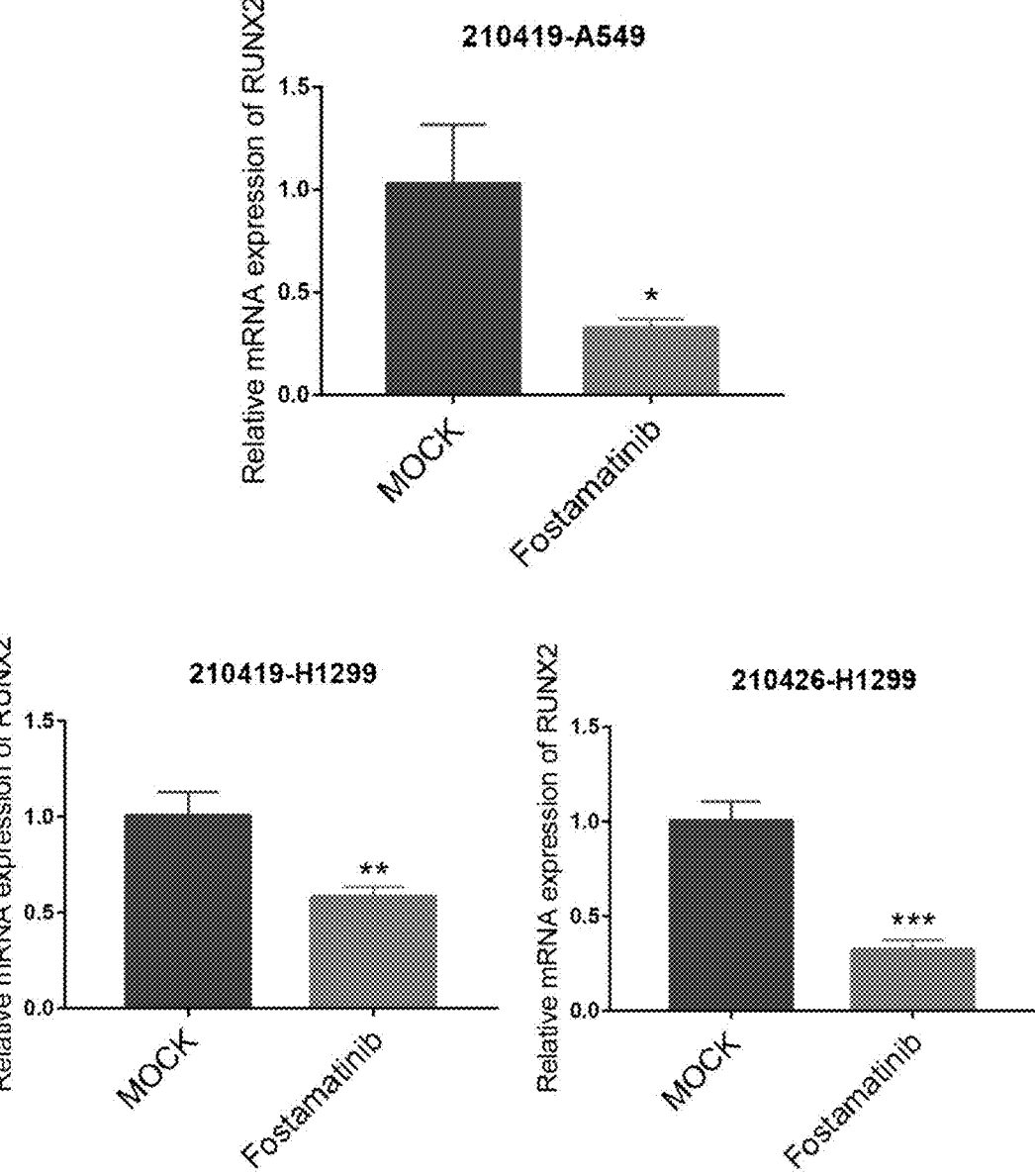
FIG. 4 shows the expression level of RUNX2 mRNA after Fostamatinib acts on lung cancer cells A549 and lung cancer cell H1299 for 6 h, respectively.

FIG. 4 shows that after Fostamatinib acts on lung cancer cells A549 and lung cancer cells H1299 for 6 hours respectively, the mRNA level of RUNX2 is significantly reduced.

Figure 5:
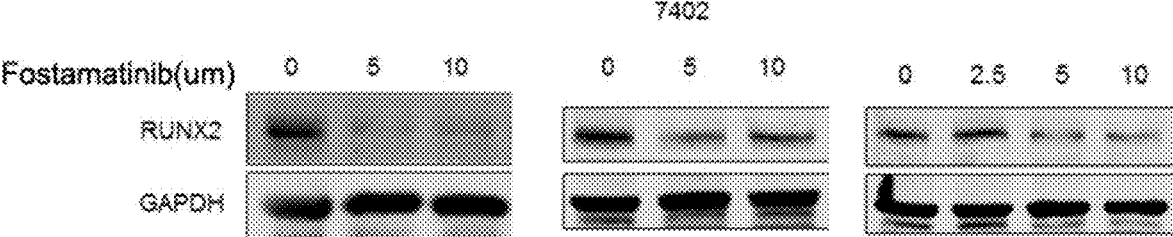
FIG. 5 shows the expression level of RUNX2 protein after treatment of BEL-7402 for 6 h in hepatoma cells with different concentrations of Fostamatinib.

FIG. 5 shows that after treating hepatoma cells BEL-7402 with 0, 2.5, 5, and 10 uM Fostamatinib for 6 h, the proteins level of hepatoma cells is significantly reduced and dose-dependent.

The above experimental results show that Fostamatinib can well inhibit the expression of mRNA of RUNX2 and has anti-tumor effects.

Animal Testing (Intraperitoneal Injection)

Drug: Fostamatinib MCE(HY-13038A)

Mice: 8-week-old C57BL/6 male mice

Concentration of administration: 40 mg/kg

Mode of administration: intraperitoneal injection

Figure 6:
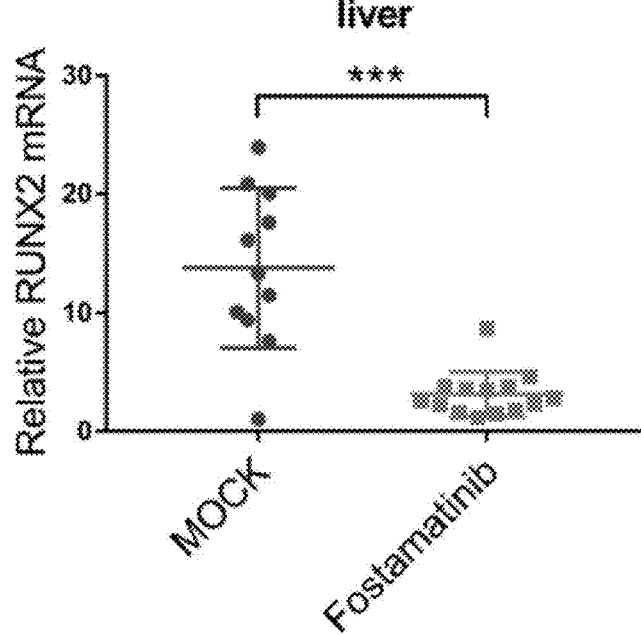
FIG. 6 shows the Effect of fostamatinib intraperitoneal injection on Runx2 mRNA expression levels in mice.

Experimental steps: mice are randomly divided into two groups, experimental group (fostamatinib) and control group (mock), before daily experiments, a certain amount of fostamatinib is accurately weighted and dissolve in 0.5% CMC (nitromethyl cellulose), fully pipetted into a uniform suspension, the concentration of 4 mg/ml, and ready for use. According to the injection volume of 100 ul/10 g per mouse, the intraperitoneal injection was carried out for 4 consecutive days. The mouse liver tissue was collected 48 hours after the last injection, RNA was extracted, and the mRNA expression level of RUNX2 was detected by real-time fluorescence quantitative PCR (qPCR). The experiment results are shown in FIG. 6. It's clear that fostamatinib can significantly reduce the mRNA expression level of RUNX2 and has anti-tumor effects.

The invention claimed is:

1. A method for treating tumor of a patient, comprising:
a) obtaining a sample from the patient with a tumor;
b) determining the level of Runx2 in the sample; and
c) diagnosing the patient as being likely to be responsive to a treatment compound if the level of Runx2 in the sample is significantly higher than a reference level of the Runx2;
d) administering to the patient in need thereof with a therapeutically effective amount of Fostamatinib or a pharmaceutically acceptable salt thereof,
   wherein the Fostamatinib or pharmaceutically acceptable salt thereof down-regulates the expression of Runx2 for treating tumor of the patient.

2. The method of claim 1, wherein said reference level of the Runx2 is the level of the Runx2 of the normal tissue of the patient.

3. The method of claim 1, wherein the pharmaceutically acceptable salt is an acid salt or a base addition salt.

4. The method of claim 1, wherein said tumor is hepatoma or lung cancer.

5. The method of claim 2, wherein said tumor is hepatoma or lung cancer.

6. The method of claim 3, wherein said tumor is hepatoma or lung cancer.

7. The method of claim 3, wherein the acid is selected from a group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, $\alpha$-ketoglutaric acid, glycolic acid, hippuric acid, hydrobromic acid, hydrochloric acid, hydroiodic acid, isethionic acid, (+)-L-lactic acid, ($\pm$)-DL-lactic acid, lactobionic acid, maleic acid, malic acid, ($-$)-L-malic acid, malonic acid, ($\pm$)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oletic acid, orotc acid, oxalic acid, palmitic acid, pamoic acid, phosphoric acid, propionic acid, L-pyroglutamic acid, salicylic acid, 4-aminosalicyl benic acid, b stearic acid, succinic acid, sulfuric acid, tannic acid, (+)-L-tartaric acid, sulfocyanic acid, p-toluenesulfonic acid, undecylenic acid, pentanoic acid, and acylated amino acid.

8. The method of claim 3, wherein the base is a hydroxide of an alkali metal or alkaline earth metal.

\* \* \* \* \*